_United States Patent_ [19]

Takahashi

[11] Patent Number: 4,545,982

[45] Date of Patent: Oct. 8, 1985

[54] PYRANONE COMPOUNDS AND SKIN-LIGHTENING COSMETIC PREPARATIONS OR LOCAL DEMELANIZING AGENTS CONTAINING THE SAME

[75] Inventor: Hidehiko Takahashi, Tokyo, Japan

[73] Assignee: Yakurigaku Chuo Kenkyusho, Tokyo, Japan

[21] Appl. No.: 358,867

[22] Filed: Mar. 17, 1982

[51] Int. Cl.$^4$ ............................................. A61K 7/135
[52] U.S. Cl. ...................................... 424/62; 549/417; 549/418; 514/460; 514/784; 514/787; 514/789
[58] Field of Search .................. 424/62, 283; 549/417, 549/418

[56] References Cited

U.S. PATENT DOCUMENTS

| | | | |
|---|---|---|---|
| 2,865,930 | 12/1958 | Metivier et al. | 424/283 X |
| 2,875,124 | 2/1959 | Gaertner et al. | 424/283 |
| 3,093,659 | 6/1963 | Bell et al. | 424/283 X |
| 3,852,444 | 12/1974 | D'Amico | 424/283 |
| 4,096,240 | 6/1978 | Mathur | 424/62 |
| 4,278,656 | 7/1981 | Nagai et al. | 424/62 |
| 4,369,174 | 1/1983 | Nagai | 424/62 |

FOREIGN PATENT DOCUMENTS

| | | | |
|---|---|---|---|
| 53-3538 | 1/1978 | Japan | 424/62 |
| 53-6432 | 1/1978 | Japan | 424/62 |
| 54-92632 | 7/1979 | Japan | 424/62 |

OTHER PUBLICATIONS

Saruno et al, Chem. Abs., 1978, vol. 88, p. 158291x.
Saruno et al, Chem. Abs., 1978, vol. 88, p. 141505x.
Kato et al, Chem. Abs., 1967, vol. 67, p. 89834d.
Takahashi, Chem. Abs., 1970, vol. 72, p. 68486e.

_Primary Examiner_—Dale R. Ore
_Attorney, Agent, or Firm_—Armstrong, Nikaido, Marmelstein & Kubovcik

[57] ABSTRACT

Novel acyl compounds 3-acyloxy-4(H)-pyran-4-ones were obtained by reacting 3-hydroxy-4(H)-pyran-4-one with acyl halides. The acyl compounds and their starting compound exhibit a skin-lightening effect on the skin and are preferably used as an active constituent in skin-lightening cosmetic preparations or local demelanizing agents.

5 Claims, 1 Drawing Figure

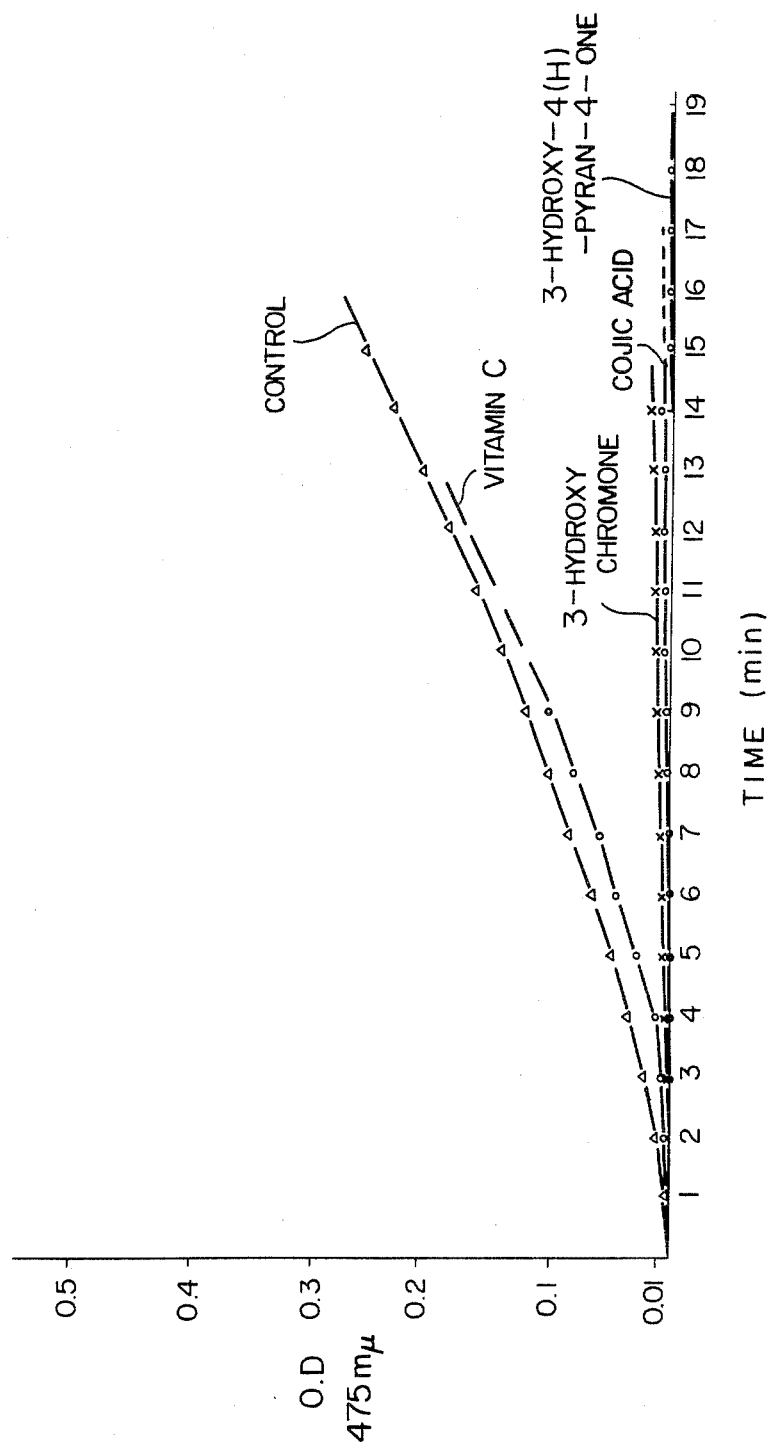

PYRANONE COMPOUNDS AND SKIN-LIGHTENING COSMETIC PREPARATIONS OR LOCAL DEMELANIZING AGENTS CONTAINING THE SAME

BACKGROUND OF THE INVENTION

This invention relates to pyranone compounds and skin-lightening (bleaching) cosmetic preparations or local demelanizing agents containing the same.

It has been a woman's desire to keep the face and skin fair and remove liver-spots caused on the face or skin. Therefore, a wide variety of substances and minerals have been used for the purpose. Cosmetic preparations and local demelanizing agents containing various peroxides, peroxy compounds such as peroxysulfates and peroxyborates or reducing agents such as vitamin C, cysteine and colloidal sulfur have been developed and used commonly even in recent years. All these substances, however, have problems related to safety and effectiveness, and satisfactory results have not been attained.

Thus, the advent of novel skin-lightening cosmetic preparations or local demelanizing agents which correct the above-mentioned disadvantages of the conventional cosmetic preparations and demelanizing agents and have the following advantages has been sought:
(a) exhibiting no toxicity to the human body;
(b) capable of remarkable skin-lightening and sunscreening effects; and
(c) positively effective against liver-spots.

SUMMARY OF THE INVENTION

The present inventors have found that the known compound 3-hydroxy-4(H)-pyran-4-one inhibits the activity of tyrosinase and exhibits remarkable inhibitory action on melanogenesis and produces an effective skin-lightening action on the human body.

The present inventors have also found that novel 3-acyloxy-4(H)-pyran-4-one compounds including acetoyloxy(acetoxy)-, palmitoyloxy(palmityloxy)- and stearoyloxy(stearyloxy)-4(H)-pyran-4-ones have similar skin-lightening effect.

BRIEF DESCRIPTION OF THE DRAWING

FIG. 1 is a graph showing the inhibitory action on tyrosinase activity of cosmetic preparations obtained by using 3-hydroxy-4(H)-pyran-4-one of the present invention and of those obtained by using vitamin C, 3-hydroxychromone and kojic acid which have been employed in the past respectively.

DETAILED DESCRIPTION OF THE INVENTION

The known compound 3-hydroxy-4(H)-pyran-4-one having the formula:

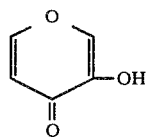

whose skin-lightening effect has been recognized by the present inventors is incorporated with various widely used fundamental cosmetic preparation bases, for example various alcohols, animal and vegetable fats, surfactants, pectin, carboxymethylcellulose, alginates as well as stabilizers, coloring matters and perfumes to provide skin-lightening cosmetic preparations or local demelanizing agents of the present invention. 3-Hydroxy-4(H)-pyran-4-one is deficient in germicidal action and antibiotic-like action, and exhibits no mutagenicity and further a weak reducing action.

Novel compounds 3-acyloxy-4(H)-pyran-4-ones having the formula:

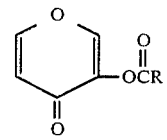

wherein R is a lower or higher alkyl group, are obtained by reacting 3-hydroxy-4(H)-pyran-4-one with acyl halides such as acetyl halides, palmitoyl (palmityl) halides or stearoyl (stearyl) halides. The acyl compounds have the advantages of not only high chemical stability and no coloring on chelating with a metal such as iron but also increased fat-solubility and good absorbability to the skin. The acyl compounds absorbed in the skin are hydrolyzed by esterase and immediately converted into the 3-hydroxy-4(H)-pyran-4-one which exhibits inhibitory action on tyrosinase activity.

The novel compounds 3-acyloxy-4(H)-pyran-4-ones are also incorporated with the above-mentioned various fundamental cosmetic preparation bases, stabilizers, coloring matters, perfumes and the like to provide the skin-lightening cosmetic preparations or local demelanizing agents of the present invention. The acyl compounds not only are deficient in germicidal action and antibiotic-like action but also exhibit no mutagenicity.

The present invention will be illustrated by citing working examples, test examples and recipe examples to which the present invention should not be limited.

WORKING EXAMPLE 1

Inhibitory action of 3-hydroxy-4(H)-pyran-4-one on tyrosinase activity

To a test tube were added 0.9 ml of a test solution, containing 40 μg of pyranone described above, which solution was obtained by adding the pyranone to 30% aqueous solution of propylene glycol; 1 ml of L-tyrosine solution (0.3 mg/ml); and 1 ml McIlvaine's buffer solution (pH 6.8), and the mixture was incubated at 37° C. for 10 minutes. 0.1 ml of a tyrosinase solution (1 mg/ml) was then added to the incubated mixture and stirred thoroughly. The absorbance at 475 mμ of the mixture was immediately measured by a spectrophotometer with time. As a control, the absorbance at 475 mμ of a 30% aqueous solution of propylene glycol instead of the above test solution was measured with time.

The 3-hydroxy-4(H)-pyran-4-one has a stronger inhibitory action on the tyrosinase activity than 3-hydroxy-chromone (chromonol) and kojic acid, and a far stronger inhibitory action than vitamin C. FIG. 1 is a graph to illustrate the effect described above, and agreement of the line showing the absorbance in the case of 3-hydroxy-4(H)-pyran-4-one with the abscissa (time) of the graph clearly indicates the remarkable effect of the 3-hydroxy-4(H)-pyran-4-one.

WORKING EXAMPLE 2

Synthesis of acetoxy-4(H)-pyran-4-one 2.2 g of 3-hydroxy-4(H)-pyran-4-one was dissolved in a mixture of 40 ml xylene with 4 ml pyridine under heating. 1.8 g of acetyl chloride was then dropped into the solution under cooling with water to form a white precipitate.

After 30 minutes, the precipitate (1.95 g) was collected and recrystallized from a mixture of water-alcohol (1:1) to give the pure acetoxy compound. The resultant filtrate was stored in an ice chamber to collect the formed precipitate, which was recrystallized from ethanol to afford 1.0 g of the acetoxy compound.

WORKING EXAMPLE 3

Synthesis of 3-palmitoyloxy-4(H)-pyran-4-one 2.2 of 3-hydroxy-4(H)-pyran-4-one was dissolved in 40 ml of pyridine. 6.6 of palmitoyl chloride was then dropped into the resultant solution under cooling with ice and stirring.

The reaction mixture was then heated at 75° C. for 5 min and allowed to stand at room temperature for another 30 min. The deposited crystal (pyrimidine hydrochloride) was removed, and the filtrate was concentrated to dryness. The recrystallization of the residue from ethanol provided 5.2 g of white crystals which were further recrystallized from 70% ethanol. The product thus obtained was identified as 3-palmitoyl-4(H)-pyran-4-one by infrared spectrophotometry.

On the other hand, the recrystallization mother liquor was concentrated to dryness, and the residue was recrystallized from a 3:7 mixture of water with ethanol to give 1.9 g of white crystals. The resultant crystals were recrystallized from 70% ethanol, and the product was identified as 3-palmitoyl-4(H)-pyran-4-one by infrared spectrophotometry.

WORKING EXAMPLE 4

Synthesis of 3-stearoyloxy-4(H)-pyran-4-one 2.2 g of 3-hydroxy-4(H)-pyran-4-one was dissolved in 40 ml of pyridine, and 6.6 g of stearoyl chloride was dropped into the resultant solution under cooling with water and stirring.

Procedures according to the synthesis of 3-palmitoyloxy-4(H)-pyran-4-one were followed to give 3-stearoyloxy-4(H)-pyran-4-one. Results of the above syntheses are summarized in the following table:

| R | Name | MP (°C.) | Calculated (%) C | Calculated (%) H | Found (%) C | Found (%) H |
|---|---|---|---|---|---|---|
| $CH_3$ | 3-Acetoxy-4(H)—pyran-4-one | 92.0 | 54.54 | 3.89 | 54.64 | 3.97 |
| $C_{15}H_{31}$ | 3-Palmitoyloxy-4(H)—pyran-4-one | 72–73 | 72.00 | 9.71 | 71.91 | 10.01 |
| $C_{17}H_{35}$ | 3-Stearoyloxy-4(H)—pyran-4-one | 43–45 | 73.00 | 10.10 | 72.46 | 10.57 |

| IR (KBr) $\nu_{max}^{KBr}\text{cm}^{-1}$ |
|---|
| 1740 (C = O), |
| 1655 (C = O) |
| 1760 (C = O), |
| 1655 (C = O) |
| 1760 (C = O), |
| 1665 (C = O) |

WORKING EXAMPLE 5

(I) Inhibitory action of 3-acyloxy-4(H)-pyran-4-ones on the tyrosinase activity

3-Acetoxy-4(H)-pyran-4-one was dissolved in ethanol, and the solution was adjusted to pH 6.0 with succinic acid or potassium carbonate to give a 1.0% 3-acetoxy-4(H)-pyran-4-one solution.

As the pretreatment, two samples (each 10 ml) were taken from the solution. To the two samples were added 1% $Na_2CO_3$ and 0.01% HCl to adjust the pH to 11.0 and 2.0, respectively. The adjusted samples were hydrolyzed by heating at 70° C. with stirring for 30 minutes.

To a test tube were added 1 ml of a L-tyrosine solution (0.3 mg/ml), 1 ml of McIlvaine's buffer solution (pH 6.8) and 0.9 ml of the 3-acetoxy-4(H)-pyran-4-one solution pretreated as described above. The mixture was incubated at 37° C. for 10 minutes, and 0.1 ml of a tyrosinase solution (1 mg/ml) was added thereto and stirred thoroughly. The absorbance at 475 mμ was immediately determined by a spectrophotometer with time. On the other hand, the absorbance of water was determined similarly with time as a control. Results similar to those of the 3-hydroxy-4(H)-pyran-4-one as shown in FIG. 1 were obtained.

(II) Enzymatic hydrolytic action of 3-acyloxy-4(H)-pyran-4-ones (1) Substrate solution: A solution containing 2% polyvinyl alcohol in M/15 phosphate buffer solution (pH 7.0) was prepared. The respective acyl compounds were added to the solution in a concentration of 0.05M and homogenized in a homogenizer to give emulsions.

(2) Enzymatic solution: 30 mg of purified bacterial lipase was dissolved in 100 ml of water. As an organic crude enzymatic solution, there was used a triturated solution of a shaved skin and pancreas of a rat weighing about 200 g.

(3) The compositions were as follows:

| Composition (ml) | A | B |
|---|---|---|
| Substrate emulsion | 5.0 | 1.0 |
| Buffer solution | 4.0 | 1.0 |
| Purified lipase | 1.0 | — |
| Triturated solution of organ | — | 2.0 |

(4) Method of measurement

The composition was incubated at 37° C. for 1 hr, and the reaction was stopped by 5% metaphosphoric acid. 0.5 ml of ferric chloride reagent (0.1% aqueous solution) was added to 5 ml of the supernatant liquid after the centrifugal precipitation to observe the coloring (wine color) thereof. The following symbols were used:

+: light wine color
++: deep wine color
+++: dark wine color
—: no coloration
±: indistinct coloration (5) Results of experiments As apparent from the following table, the acyl compounds are subjected to enzymatic hydrolysis.

| Substrate (Acyl compounds) | Ratio of formation of 3-hydroxy-4(H)—pyran-4-one | | |
|---|---|---|---|
| | Bacterial lipase (purified) | Homogenate | |
| | | Rat's skin | Rat's pancreas |
| Acetoxy compound | + | +++ | +++ |
| Palmitoyl compound | ± | ++ | ++ |

WORKING EXAMPLE 6

Action of 3-hydroxy-4(H)-pyran-4-one and acyl derivatives thereof on the melanization in the human skin.

The test substance was mixed and dissolved in a hydrophilic ointment according to the Japanese Pharmacopoeia and applied to a melasma on one side of each human face 3 times a day. The effect was observed by the naked eye to obtain the results shown in the following table. In the control, only the hydrophilic ointment was applied to a melasma on the other side of the human face in the similar way.

| Test ointment | Application period | Number of volunteer |
|---|---|---|
| | months | |
| Pharmacopoeial hydrophilic ointment | 3 | 15 |
| Hydrophilic ointment containing 1% 3-hydroxy-4(H)—pyran-4-one | 3 | 10 |
| Hydrophilic ointment containing 0.5% 3-hydroxy-4(H)—pyran-4-one | 3 | 10 |
| Hydrophilic ointment containing 2% 3-palmitoyloxy-4(H)—pyran-4-one | 3 | 10 |
| Hydrophilic ointment containing 1% 3-palmitoyloxy-4(H)—pyran-4-one | 3 | 10 |
| Hydrophilic ointment containing 0.5% 3-palmitoyloxy-4(H)—pyran-4-one | 3 | 10 |

Note:
"Effective" indicates the distinct removal of black color, and "Remarkably effective" indicates almost the disappearance of melanin.

| | Results | |
|---|---|---|
| Ineffective | Effective | Remarkably effective |
| 15 | 0 | 0 |
| 0 | 2 | 8 |
| 2 | 3 | 5 |
| 0 | 2 | 8 |
| 0 | 4 | 6 |
| 3 | 2 | 5 |

Recipe examples of the present invention will be enumerated hereafter; however, the present invention should not be limited only thereto.

| Recipe 1 [lotion] (Component) | % by weight |
|---|---|
| 3-Hydroxy-4(H)—pyran-4-one or 3-acetoxy-4(H)—pyran-4-one | 0.1 0.5 |

-continued

| Recipe 1 [lotion] (Component) | % by weight |
|---|---|
| Aminoacetic acid | 0.2 |
| Pyridoxine hydrochloride | 0.05 |
| Zinc phenolsulfonate | 0.3 |
| Propylene glycol | 10.0 |
| Ethanol | 30.0 |
| Perfume and preservative | Small quantity |
| Purified water | Balance |

| Recipe 2 [pack] (Component) | % by weight |
|---|---|
| 3-Palmitoyloxy-4(H)—pyran-4-one | 0.5–1.0 |
| Stearic acid | 4.0 |
| Aminoacetic acid | 0.2 |
| Zinc phenolsulfonate | 0.3 |
| Propylene glycol | 13.0 |
| Carboxy vinyl polymer | 1.2 |
| Emulsifier | 3.0 |
| Ethanol | 2.5 |
| Titanium oxide | 0.02 |
| Perfume and preservative | Small quantity |
| Purified water | Balance |

| Recipe 3 [milk lotion] (Component) | % by weight |
|---|---|
| 3-Palmitoyloxy-4(H)—pyran-4-one (or 3-stearoyloxy-4(H)—pyran-4-one) | 1.0 |
| Stearic acid | 2.0 |
| Cetanol | 0.5 |
| Lanolin | 2.0 |
| Oleyl oleate | 2.0 |
| Squalane | 3.0 |
| Liquid paraffin | 8.0 |
| Emulsifier | 2.6 |
| Propylene glycol | 4.0 |
| Perfume, antioxidant and preservative | Small quantity |
| Purified water | Balance |

| Recipe 4 [vanishing cream] (Component) | % by weight |
|---|---|
| 3-Palmitoyloxy-4(H)—pyran-4-one | 1.0 |
| MC stearic acid | 8.0 |
| Beeswax | 5.0 |
| Cetanol | 3.0 |
| Lanolin | 2.0 |
| Isopropyl myristate | 6.0 |
| Liquid paraffin | 7.0 |
| Olive oil | 2.0 |
| Emulsifier | 5.5 |
| Propylene glycol | 3.0 |
| Perfume, antioxidant and preservative | Small quantity |
| Purified water | Balance |

| Recipe 5 [cold cream] (Component) | % by weight |
|---|---|
| 3-Hydroxy-4(H)—pyran-4-one | 0.5 |
| Beeswax | 10.0 |
| Ceresin | 7.0 |
| White petrolatum | 3.0 |
| Lanolin | 3.0 |
| Isopropyl myristate | 3.0 |
| Squalane | 4.0 |
| Liquid paraffin | 40.0 |
| Polyoxyethylene cetyl ether | 2.7 |
| Emulsifier | 2.3 |

-continued

| Recipe 5 [cold cream] (Component) | % by weight |
|---|---|
| Propylene glycol | 2.0 |
| Perfume, antioxidant and preservative | Small quantity |
| Purified water | Balance |

What is claimed is:

1. 3-acyloxy-4(H)-pyran-4-one compounds having the formula:

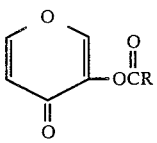

wherein R is an alkyl group having 1–17 carbon atoms.

2. Compounds of claim 1, wherein R is selected from the group consisting of $CH_3$, $C_{15}H_{31}$ and $C_{17}H_{35}$.

3. A method for skin lightening comprising applying to the skin an aqueous composition in the form of lotions, creams, packs, milk lotions, or ointments, said composition comprising an effective skin lightening amount of at least one active ingredient selected from the group consisting of 3-hydroxy-4(H)-pyran-4-one having the formula:

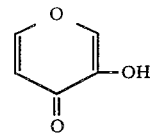

and 3-acyloxy-4(H)-pyran-4-one compounds having the formula:

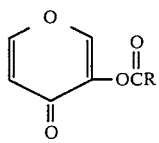

wherein R is an alkyl group having 1–17 carbon atoms.

4. The method for skin lightening of claim 3, wherein R is selected from the group consisting of $CH_3$, $C_{15}H_{31}$ and $C_{17}H_{35}$.

5. The method for skin lightening of claim 3, wherein the aqueous composition contains 0.002 to 5% by weight, preferably 0.01 to 1% by weight, of said active ingredient.

* * * * *